(12) United States Patent
Venugopal et al.

(10) Patent No.: US 7,019,844 B2
(45) Date of Patent: *Mar. 28, 2006

(54) METHOD FOR IN-SITU MONITORING OF PATTERNED SUBSTRATE PROCESSING USING REFLECTOMETRY.

(75) Inventors: Vijayakumar C. Venugopal, Berkeley, CA (US); Andrew J. Perry, Fremont, CA (US)

(73) Assignee: Lam Research Corporation, Fremont, CA (US)

( * ) Notice: Subject to any disclaimer, the term of this patent is extended or adjusted under 35 U.S.C. 154(b) by 321 days.

This patent is subject to a terminal disclaimer.

(21) Appl. No.: 10/286,410

(22) Filed: Nov. 1, 2002

(65) Prior Publication Data

US 2004/0032592 A1    Feb. 19, 2004

Related U.S. Application Data

(60) Provisional application No. 60/408,619, filed on Sep. 6, 2002, provisional application No. 60/403,213, filed on Aug. 13, 2002.

(51) Int. Cl.
*G01B 9/02*    (2006.01)
(52) U.S. Cl. ........................................... 356/504
(58) Field of Classification Search ........... 356/503, 356/504
See application file for complete search history.

(56) References Cited

U.S. PATENT DOCUMENTS

| 4,147,435 | A | * | 4/1979 | Habegger ............... 356/503 |
|---|---|---|---|---|
| 5,900,633 | A | | 5/1999 | Solomon et al. |
| 5,936,734 | A | | 8/1999 | Johs et al. |
| 5,980,768 | A | | 11/1999 | Abraham |
| 6,111,634 | A | | 8/2000 | Pecen et al. |
| 6,136,712 | A | | 10/2000 | Klippert et al. |
| 6,160,621 | A | | 12/2000 | Perry et al. |
| 6,271,047 | B1 | | 8/2001 | Ushio et al. |
| 6,275,297 | B1 | | 8/2001 | Zalicki |
| 6,410,451 | B1 | | 6/2002 | Nguyen et al. |
| 6,413,867 | B1 | | 7/2002 | Sarfaty et al. |
| 6,567,213 | B1 | | 5/2003 | Rosencwaig et al. |
| 6,589,869 | B1 | | 7/2003 | Sarfaty et al. |

(Continued)

FOREIGN PATENT DOCUMENTS

EP        1111356 A2    6/2001

(Continued)

OTHER PUBLICATIONS

PCT International Search Report, EPO, PCT/US03/25147.

(Continued)

*Primary Examiner*—Gregory J. Toatley, Jr.
*Assistant Examiner*—Michael A. Lyons
(74) *Attorney, Agent, or Firm*—IP Strategy Group, PC (57) ABSTRACT

A method of determining a parameter of interest during fabrication of a patterned substrate includes illuminating at least a portion of the patterned substrate with a normal incident light beam, obtaining a measured net reflectance spectrum of the portion of the patterned substrate from a normal reflected light beam, calculating a modeled net reflectance spectrum of the portion of the patterned substrate, and determining a set of parameters that provides a close match between the measured net reflectance spectrum and the modeled net reflectance spectrum. The modeled net reflectance spectrum is calculated as a weighted incoherent sum of reflectances from $n \geq 1$ different regions constituting the portion of the patterned substrate, wherein the reflectance of each of the n different regions is a weighted coherent sum of reflected fields from $k \geq 1$ laterally-distinct areas constituting the region.

22 Claims, 7 Drawing Sheets

U.S. PATENT DOCUMENTS

| | | |
|---|---|---|
| 6,608,681 B1 | 8/2003 | Tanaka et al. |
| 6,673,637 B1 | 1/2004 | Wack et al. |
| 2004/0087041 A1* | 5/2004 | Perry et al. ............. 438/5 |

FOREIGN PATENT DOCUMENTS

| | | |
|---|---|---|
| JP | 2000292129 | 10/2000 |
| US | 02/90743 | 7/2002 |

OTHER PUBLICATIONS

Hicks et al., "Reflectance Modeling for In Situ Dry Etch Monitoring of Bulk $SiO_2$ and III-V multilayer structures" (Nov. 1994) Jrnl of Vac. Sc. & Tech. pp. 3306-3310.

Bosch-Charpenay et al., "Real-Time Etch-Dept Measurements of MEMS Devices" (Apr. 2002) Jrnl of MicroElect. Sys., IEEE, NY, pp. 113-117.

Benson et al., "In-situ Spectroscopic Reflectometry for Polycrystalline Silicon Thin Film Etch Rate Determination during Reactive Ion Etching", (Jun. 1996) Jrnl of Elect. Mat., pp. 955-964.

Anon., "Zero-Order reflecting Reference Optics", (Jan. 1990) IBM Tech. Discl. Bulletin, pp. 381-383.

PCT International Search Report, PCT/US03/25146, dated Feb. 20, 2004.

P.A. Heimann and R.J. Schutz, "Optical etch-rate monitoring: computer simulation of reflectance," J. Electrochem. Soc. 131, pp. 881-885 (1984).

P.A. Heinmann, "Optical etch-rate monitoring using active device areas: lateral interference effects," J. Electrochem. Soc. 132, pp. 2003-2006 (1985).

H.L. Maynard, N. Layadi, and J.T.-C. Lee, "Multiwavelength ellipsometry for real-time process control of the plasma etching of patterned samples," J. Vac. Sci. Technol. B 15, pp. 109-115 (1997).

W. Kong, H.-T. Huang, and F. L. Terry, Jr., "A hybrid analysis of ellipsometry data from patterned structures," Proceedings of NIST 2000, AIP Conference Proceedings, v. 550, pp. 373-377 (2001).

P. Lalanne and D.L. Lalanne, "On the effective medium theory of subwavelenght periodic structures," J. Mod. Opt. (1996).

V. C. Venugopal, A. Lakhtakia, R. Messier, and J.-P. Kucera, "Low permittivity nonocomposite materials using sculptured thin film technology," J. Vac. Sci. Technol. A 18, pp. 32-36 (2000).

G. Bouchitte and R. Petit, "Homogenization techniques as applied in the electromagnetic theory of gratings," Electromagnetics 5, pp. 17-36 (1985).

Z. R. Hatab, J.R. McNeil, and S. S. H. Naqvi, "Sixteen-megabit dynamic random access memeory trench depth characterization using two-dimensional diffraction analysis," J. Vac. Sci. Technol. B 13, pp. 174-182 (1995).

H. Kikuta, Y. Ohira, H. Kubo, and K. Iwata, "Effective medium theory of two-dimensional subwavelength gratings in the non-quasi-static limit," J. Opt. Soc. of A., vol. 15, No. 6, pp. 1577-1585 (Jun. 1998).

J.P. Merceron, V.C. Venugopal, A.J. Perry, and A.J. Miller, "Endpoint Strategies for Recess Processes in DRAM and eDRAM Applications," Abstract 1253, AVS 49th International Symposium (Nov. 2002).

S. Zaidi, G. Stojakovic, A. Gutmann, C. Bozdog, U. Mantz, S. B. Charpenay, and P. Rosenthal, "FTIR-based non-destructive method for metrology of depths in poly silicon filled trenches," *Metrology, Inspection, and Process Control for Microlithography XVII*, Daniel J. Herr (ed.), Proceedings of SPIE, vol. 5038, pp. 185-190 (2003).

C. G. Galarza, P. P. Khargonekar, F. L. Terry, Jr., "Real-time estimation of patterned wafer parameters using in-situ spectroscopic ellipsometry," Proceedings of the 1999 IEEE, International Conference on Control Applications, Hawaii, pp. 773-778 (Aug. 1999).

J. Merceron, "Robust endpoint strategies for recess processes," Ecole Polytechnique Promotion X99, pp. 1-28 (2002).

B. Michel, "Recent developments in the homogenization of linear bianisotropic composite materials," *Electromagnetic Fields in Unconventional Materials and Structures* (Chapter 2), Singh and Lakhtakia (ed.), John Wiley and Sons, Inc., pp. 39-83 (2000).

P.-Y. Guittet, U. Mantz, P. Weidner, J.-L. Stehle, S. Bourtault, and D. Zahorski, "Infrared Spectroscopic el-lipsometry in semiconductor manufacturing," *Metrology, Inspection, and Process Control for Microlithography XVIII*, R. M. Silver (ed.), Proceedings of SPIE, vol. 5375, pp. 771-778 (May 2004).

A. Dag, V. M. Rubinstein, Y. Gilboa, S. Hedayati, "Performing STI process control using large-spot-size fourier-transform reflectometry," micromagazine.com, pp. 25-30 (Apr. 2003).

C. F. Bohren and D. R. Huffman, *Absorption and Scattering of Light by Small Particles* Wiley Science Paperback Series, John Wiley and Sons, Inc., pp. 212-219 (1983).

A. Lakhtakia (ed.), *Selected Papers on Linear Optical Composite Materials*, Milestone vol. 120, Bellingham, WA: SPIE Optical Engineering Press (1996).

J.N. Mait and D. W. Prather (eds.), *Selected Papers on Subwavelength Diffractive Optics*, Milestone vol. 166, Bellingham, WA: SPIE Optical Engineering Press (2001).

U.S. Appl. No. 10/401,118, filed Mar. 27, 2003, "Process Endpoint Detection Method Using Broadband Reflectometry".

U.S. Appl. No. 10/286,409, filed Nov. 1, 2002, "Method for controlling a recess etch process".

* cited by examiner

METHOD FOR IN-SITU MONITORING OF PATTERNED SUBSTRATE PROCESSING USING REFLECTOMETRY.

CROSS REFERENCE TO RELATED APPLICATIONS

This application claims priority from and incorporates by reference the following provisional application(s) entitled "Endpoint Strategies for in situ Control of Recess and Deep Trench Etch Processes," filed "Aug. 13, 2002" (Application No. 60/403,213) by inventor(s) Vijayakumar C. Venugopal and Andrew J. Perry and "Reflectrometry-based Approaches For in situ Monitoring of Etch Depths in Plasma Etching Processes," filed Sep. 6, 2002 (Application No. 60/408,619) by inventor(s) Vijay C. Venugopal and Andrew J. Perry.

BACKGROUND OF THE INVENTION

The invention relates generally to methods for monitoring and controlling processes used in forming features on patterned substrates. More specifically, the invention relates to an optical diagnostic method for detecting an endpoint in patterned substrate processing.

In semiconductor manufacturing, various combinations of processes such as etching, thin-film deposition, and chemical-mechanical polishing are used to form features on a patterned substrate. The features are formed by selectively removing materials from and selectively depositing materials on the surface of the patterned substrate. While forming the features, the patterned substrate is monitored to determine when an endpoint has been reached in the process. An endpoint could be a point at which the process conditions should be changed or a point at which the process should be stopped.

The ability to accurately detect an endpoint while processing a patterned substrate is becoming increasingly important as pattern geometries shrink and dimensional control on small feature sizes become increasingly stringent. For etching processes, the ability to accurately detect an endpoint is crucial when the layers of materials to be removed from the patterned substrate are very thin and/or some of the layers on the substrate must remain substantially unaffected after processing of the substrate. For example, in gate etch processes, multiple layers of materials must be removed without damaging the gate oxide layer.

Optical diagnostic methods are typically used to detect endpoints in patterned substrate processing because they are non-intrusive. Optical emission spectroscopy is one example of an optical diagnostic method that detects an endpoint by monitoring emissions from a plasma. The plasma emissions are monitored for the presence or absence of one or more active species. The response of this method is usually delayed because it detects the plasma state instead of the substrate state. Thus, optical emission spectroscopy is generally unsuitable for etching applications where a sacrificial layer that marks an etching endpoint is absent or where an effective etch stop layer is so thin that the chances of etching through it prior to detection of the active species in the plasma is fairly high.

Single-wavelength interferometry is an example of an optical diagnostic method that detects an endpoint by monitoring relative changes in the vertical dimensions of features on the patterned substrate. The method involves directing a narrow light beam onto the substrate surface and measuring the intensity of the beam reflected from the substrate surface. The basic assumption in this method is that the intensity of the reflected beam varies primarily as a result of changes in the feature of interest. By monitoring modulation of the reflected beam, the relative changes in the vertical dimension of the feature of interest can be determined. Because single-wavelength interferometric approaches monitor relative changes in vertical dimensions of features as opposed to absolute vertical dimensions of the features, they are limited in their ability to compensate for incoming material variations, such as variation in thickness of layers formed on substrates, variation in starting depth of trenches, variation in pattern densities, and variation in wafer orientation.

Spectroscopic ellipsometry, polarimetry, and reflectometry are examples of optical diagnostic methods that can be used in conjunction with rigorous optical modeling techniques to determine the absolute vertical and lateral dimensions of features of special test structures such as one-dimensional gratings on a patterned substrate. However, these techniques are limited to in-line metrology applications (i.e., pre- and post-processing metrology) rather than in-situ diagnostics since they involve measurements only on special test structures and also a significant computational load. Efforts have been made to combine the use of spectroscopic ellipsometry and simple, considerably less accurate, modeling techniques for in-situ diagnostics.

From the foregoing, there is desired a robust, easy-to-use, and accurate method for in-situ diagnostics that will facilitate detecting an endpoint in patterned substrate processing without any special test structure requirements.

SUMMARY OF THE INVENTION

In one aspect, the invention relates to a method of determining a parameter of interest during fabrication of a patterned substrate. The method comprises illuminating at least a portion of the patterned substrate with a normal incident light beam and obtaining a measured net reflectance spectrum of the portion of the patterned substrate from a normal reflected light beam. The method further includes calculating a modeled net reflectance spectrum of the portion of the patterned substrate as a weighted incoherent sum of reflectances from $n \geq 1$ different regions constituting the portion of the patterned substrate, wherein the reflectance of each of the n different regions is a weighted coherent sum of reflected fields from $k \geq 1$ laterally-distinct areas constituting the region. The method further includes determining a set of parameters that provides a close match between the measured net reflectance spectrum and the modeled net reflectance spectrum.

In another aspect, the invention relates to a process control method for fabrication of a patterned substrate. The process control method comprises illuminating at least a portion of the patterned substrate with a normal incident light beam while processing the patterned substrate and obtaining a measured reflectance spectrum of the portion of the patterned substrate over a range of wavelengths. The process control method further includes calculating a modeled reflectance spectrum of the portion of the patterned substrate over a range of wavelengths as a weighted incoherent sum of reflectances from $n \geq 1$ different regions constituting the patterned substrate, wherein the reflectance of each of the n different regions is a weighted coherent sum of reflected fields from $k \geq 1$ laterally-distinct areas constituting the region. The process control method further includes determining a set of parameters that provides a close match between the measured reflectance spectrum and the modeled reflectance spectrum, deriving a parameter of interest from the set of parameters, and signaling an endpoint in the processing of the patterned substrate if the value of the parameter of interest satisfies a predetermined endpoint criterion.

In yet another aspect, the invention relates to a method for determining a vertical dimension of a feature on a patterned substrate. The method comprises illuminating at least a portion of the patterned substrate including the feature with a normal incident light beam and obtaining a measured net reflectance spectrum of the portion of the patterned substrate from a normal reflected light beam. The method further includes calculating a modeled net reflectance spectrum of the portion of the patterned substrate as a weighted incoherent sum of reflectances from $n \geq 1$ different regions constituting the portion of the patterned substrate, wherein the reflectance of each of the n different regions is a weighted coherent sum of reflected fields from $k \geq 1$ laterally-distinct areas constituting the region. The method further includes determining a set of parameters that provides a close match between the measured reflectance spectrum and the modeled net reflectance spectrum and extracting the vertical dimension of the feature from the set of parameters.

These and other features and advantages of the invention will be discussed in more detail in the following detailed description of the invention and in conjunction with the following figures.

BRIEF DESCRIPTION OF THE DRAWINGS

The invention is illustrated by way of example, and not by way of limitation, in the figures accompanying the drawings, and in which like reference numerals refer to similar elements, and in which.

DETAILED DESCRIPTION OF THE PREFERRED EMBODIMENTS

The invention will now be described in detail with reference to a few preferred embodiments, as illustrated in the accompanying drawings. In the following description, numerous specific details are set forth in order to provide a thorough understanding of the invention. It will be apparent, however, to one skilled in the art, that the invention may be practiced without some or all of these specific details. In other instances, well-known process steps and/or features have not been described in detail in order to not unnecessarily obscure the invention. The features and advantages of the invention may be better understood with reference to the drawings and discussions that follow.

In one embodiment, the invention uses reflectometry to measure a reflectance spectrum of a patterned substrate while the patterned substrate is being processed. For each given time step, physical parameters of interest are estimated by matching the measured reflectance spectrum to a modeled reflectance spectrum of the patterned substrate. In accordance with one embodiment of the invention, there is provided a model for calculating the reflectance spectrum of the patterned substrate. Advantageously, the model does not place any restrictions on arrangement of features on the patterned substrate, i.e., the model is not limited to a patterned substrate having special test features and can be applied to a patterned substrate having a complex array of random features. Furthermore, the model is also designed to accommodate incoming material variations.

Figure 1:
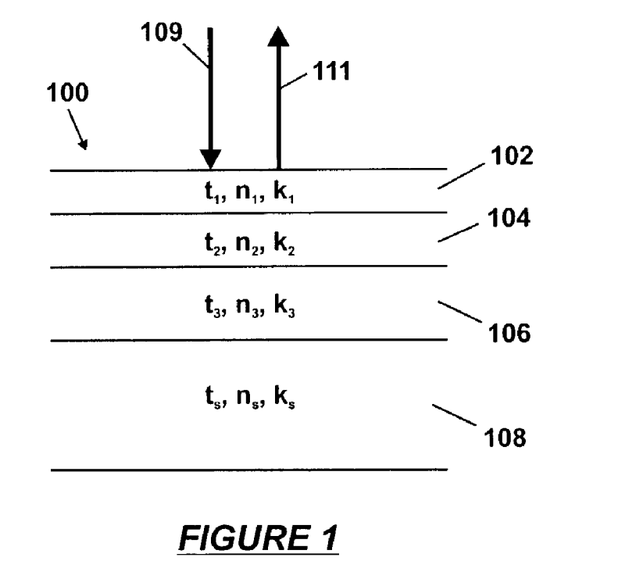
FIG. 1 is a generalized schematic of a thin-film stack.

While not wishing to be bound by theory, the inventors believe herein that a patterned substrate can be divided into n laterally-distinct areas and that each distinct area can be modeled as an isotropic, homogeneous thin-film stack. For illustration purposes, FIG. 1 shows a thin-film stack 100 having a stack of three thin-film layers 102, 104, 106 on a substrate layer 108. Each of the layers 102, 104, 106, 108 has a thickness (t), a refractive index (n), and an extinction coefficient (k). Reflectance measurements are made by illuminating the thin-film stack 100 at normal incidence with a light beam 109 and collecting the light beam 111 reflected normally from the thin-film stack 100. For normal incidence reflectometry, the response of an isotropic, homogeneous thin-film stack is nominally polarization-independent. Given the random array of structure sizes and orientations that constitute a typical pattern on a semiconductor substrate, the inventors believe herein that the patterned substrate can be assumed to have a nominally polarization-independent reflectance, which greatly simplifies the computational aspects of the model. It must be noted, however, that the technique can be easily adapted to model a polarization-dependent response too. For example, this may indeed be the case when the distribution of structures constituting the pattern is known to be predominantly oriented in one direction within the plane of the patterned substrate.

Figure 2A:
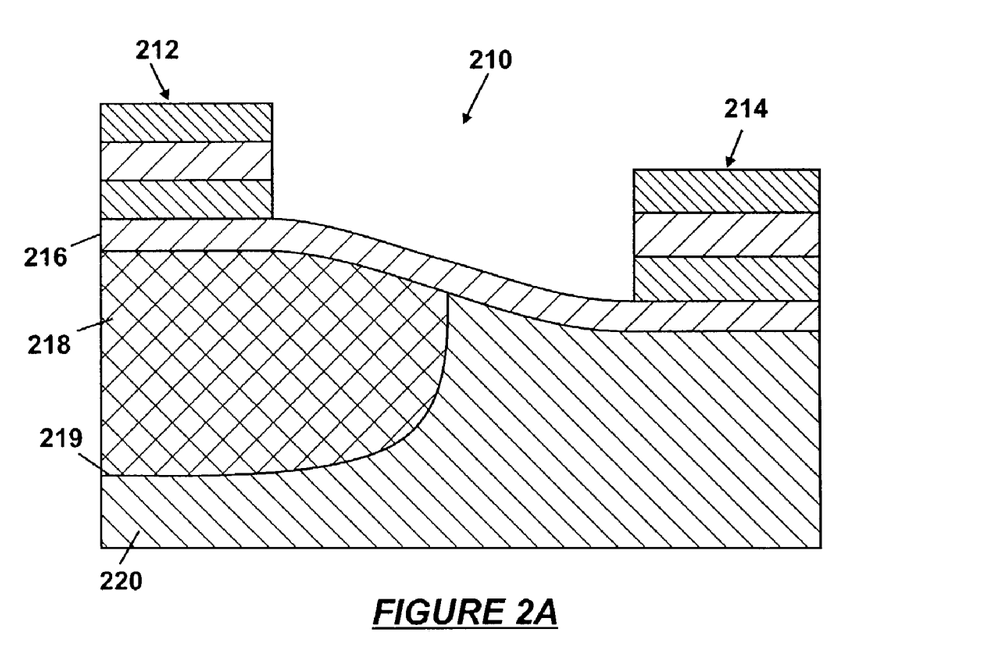
FIG. 2A shows a transverse cross-section of a typical patterned substrate.

The main factors defining lateral distinctness are differences in layers constituting the thin-film stacks and differences in heights of the thin-film stacks. For illustration purposes, FIG. 2A shows a transverse cross-section of a typical patterned substrate 210, e.g., a gate wafer, having stacks of thin-film layers 212, 214 formed on a gate oxide layer 216. A relatively thick field oxide layer 218, which is used for electrical isolation, underlies a portion of the gate oxide layer 216. The field oxide layer 218 is formed by etching a shallow trench 219 into a silicon substrate 220, overfilling the trench 219 with an oxide or other dielectric material, and planarizing the overfill using, for example, a chemical-mechanical polishing process. The patterned substrate 210 can be divided into four laterally-distinct areas or thin-film stacks based on the number of thin-film layers in the stacks 212, 214 and the lateral extent of the field oxide layer 218.

Figure 2B:
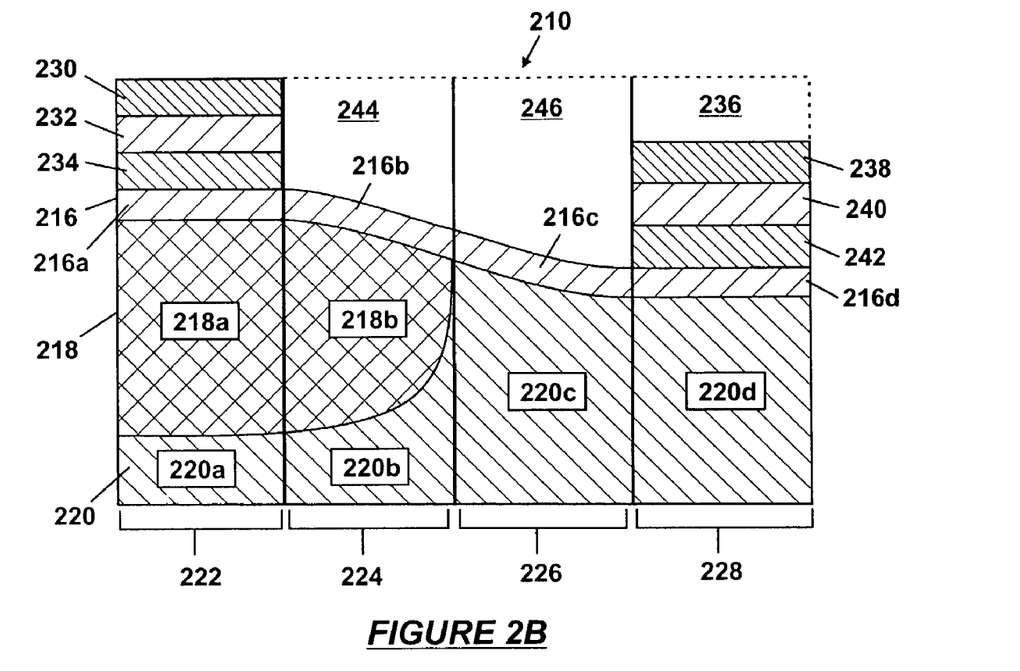
FIG. 2B shows the patterned substrate of FIG. 2A divided into four laterally-distinct areas or thin-film stacks.

FIG. 2B shows the patterned substrate 210 divided into four distinct areas 222, 224, 226, 228. The distinct area 222 includes thin-film layers 230, 232, 234, a portion 216a of the gate oxide layer 216, a portion 218a of the field oxide layer 218, and a portion 220a of the substrate 220. As an example, the thin-film layers 230, 232 could be mask layers and the thin-film layer 234 could be a polysilicon layer. The distinct area 224 includes a portion 216b of the gate oxide layer 216, a portion 218b of the field oxide layer 218, and a portion 220b of the substrate 220. The distinct area 226 includes a portion 216c of the gate oxide layer 216 and a portion 220c of the substrate 220. The distinct area 228 includes thin-film layers 238, 240, 242, a portion 216d of the gate oxide layer 216, and a portion 220d of the substrate 220. The layers 230 and 238 are the same material and, nominally, have the same thickness. Similarly, the layer 232 corresponds to layer 240, and the layer 234 corresponds to layer 242.

The reflectance of the patterned substrate 210 is a combination of the reflected fields from the thin-film stacks 222, 224, 226, 228. The reflected field for a given thin-film stack illuminated by a plane wave of known intensity and polarization can be calculated by setting up and solving a boundary value problem or by using Fresnel equations. For the purpose of calculating reflectance, differences in the heights of the thin-film stacks 222, 224, 226, 228 may be compensated for by adding layers of air or vacuum, equal in thickness to the difference in height with respect to the highest thin-film stack structure on the substrate, to the top of the thin-film stack. For example, a layer of air or vacuum 244 is added to the film stack 224, a layer of air or vacuum 246 is added to the film stack 226, and a layer of air or vacuum 236 is added to the film stack 228 to make the heights of the film stacks 222, 224, 226, and 228 uniform.

The inventors believe herein that given the wide distribution of the lateral extents of features constituting a typical patterned substrate, the reflected fields from the patterned substrate are likely to add coherently over some regions of the pattern and incoherently over some other regions of the pattern. The inventors believe herein that the relative contributions of the coherently and incoherently combined fields could vary as a function of free-space wavelength, $\lambda_0$, and do not necessarily correspond to the actual area fractions on the patterned substrate. Thus, once the reflected fields from each distinct thin-film stack have been calculated, the net reflectance from a patterned substrate can be calculated as a weighted incoherent sum of reflectances from n different regions constituting the pattern:

$$R = w_1(\lambda_0)|E_1|^2 + w_2(\lambda_0)|E_2|^2 + \ldots + w_n(\lambda_0)|E_n|^2 \quad (1)$$

where R is the net reflectance measured, $E_i$ are the individual incoherently adding field terms, and $w_i(\lambda_0)$ are the weighting factors for the incoherently adding terms. The use of $|E_i|^2$ denotes the magnitude of the complex field $E_i$ in the frequency domain notation of electromagnetic field theory.

Figure 3:
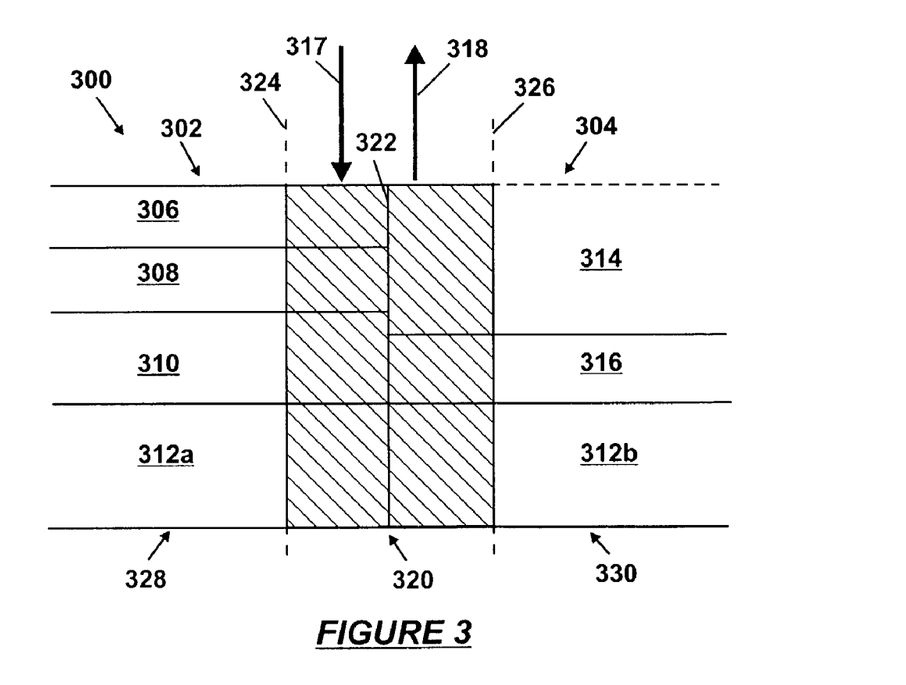
FIG. 3 shows a patterned substrate divided into two laterally-distinct areas or thin-film stacks.

Each individual incoherently adding term in equation (1) above could be the weighted, coherent sum of fields from k laterally-distinct areas constituting the $i^{th}$ region on the substrate:

$$E_i = \alpha_1(\lambda_0)E_{c1} + \alpha_2(\lambda_0)E_{c2} + \ldots + \alpha_k(\lambda_0)E_{ck} \quad (2)$$

where $\alpha_i(\lambda_0)$ are the weighting factors for coherently adding field terms $E_{ci}$. It should be noted that a "region" is not the same as a "distinct area." To further illustrate this concept, consider the patterned substrate 300 shown in FIG. 3. The patterned substrate 300 has been divided into two laterally-distinct areas or thin-film stacks 302, 304. The thin-film stack 302 is made of thin-film layers 306, 308, 310 and a portion 312a of a substrate 312. The thin-film stack 304 is made of a layer of air or vacuum 314, a thin-film layer 316, and a portion 312b of the substrate 312.

In operation, an incident beam 317 illuminates the patterned substrate 300 and is reflected, as shown at 318. Let $r_1$ represent the reflected field due to the thin-film stack 302 and $r_2$ represent the reflected field due to the thin-film stack 304. The inventors propose herein that there is a region 320 overlapping the boundary 322 between the thin-film stacks 302, 304, demarcated by imaginary lines 324, 326, where the reflected fields $r_1$ and $r_2$ would add coherently because of lateral interference effects. The reflectance from the region 328 to the left of the imaginary line 324 is expected to be due to the reflected field from the thin-film stack 302 only. The reflectance from the region 330 to the right of the imaginary line 326 is expected to be due to the reflected field from the thin-film stack 304 only.

From equation (1), the net reflectance from the patterned substrate 300 is:

$$R_{300} = w_{328}(\lambda_0)|E_{328}|^2 + w_{320}(\lambda_0)|E_{320}|^2 + w_{330}(\lambda_0)|E_{330}|^2 \quad (3)$$

where $R_{300}$ is the net reflectance from the patterned substrate 300, $E_{328}$, $E_{320}$, $E_{330}$ are the individual incoherently adding field terms from the regions 328, 320, 330, respectively, and $w_{328}(\lambda_0)$, $w_{320}(\lambda_0)$, $w_{330}(\lambda_0)$ are the weighting factors for the incoherently adding terms. From equation (2), $E_{320}$ is:

$$E_{320} = \alpha(\lambda_0)E_{328} + (1 - \alpha(\lambda_0))E_{330} \quad (4)$$

It should be noted that $E_{328}$ is $r_1$, $E_{330}$ is $r_2$, and $w_{330}$ can be rewritten as $(1 - w_{328} - w_{320})$. Thus, equation (3) can be rewritten as:

$$R_{300} = w_{328}|r_1|^2 + w_{320}|\alpha r_1 + (1-\alpha)r_2|^2 + (1 - w_{320} - w_{328})|r_2|^2 \quad (5)$$

where the terms $w_{328}$, $w_{320}$, and $\alpha$ could vary as a function of free-space wavelength, $\lambda_0$.

Equation (1) provides a simplified model wherein reflectance from a patterned substrate can be parameterized with respect to several quantities of interest, such as film thicknesses and etch depths. In one embodiment, the invention uses normal incidence reflectometry as a technique for measuring reflectance, meaning the patterned substrate is illuminated by a beam incident normal to the substrate and only the light reflected normal to the substrate is collected, i.e., only specularly reflected light is collected. However, because a range of orientations can be seen in any pattern, not all of the light illuminating the pattern will reflect at normal incidence. There will be non-specular reflection due to, for example, sloped walls and rounded or faceted lines. Reflection losses due to such non-specular reflection should not be ignored. In an embodiment of the invention, a scattering loss factor is applied to parts of the adding terms in equation (1) or to the entire reflectance in equation (1). The scattering loss factor could be a function of $\lambda_0$.

Figure 4:
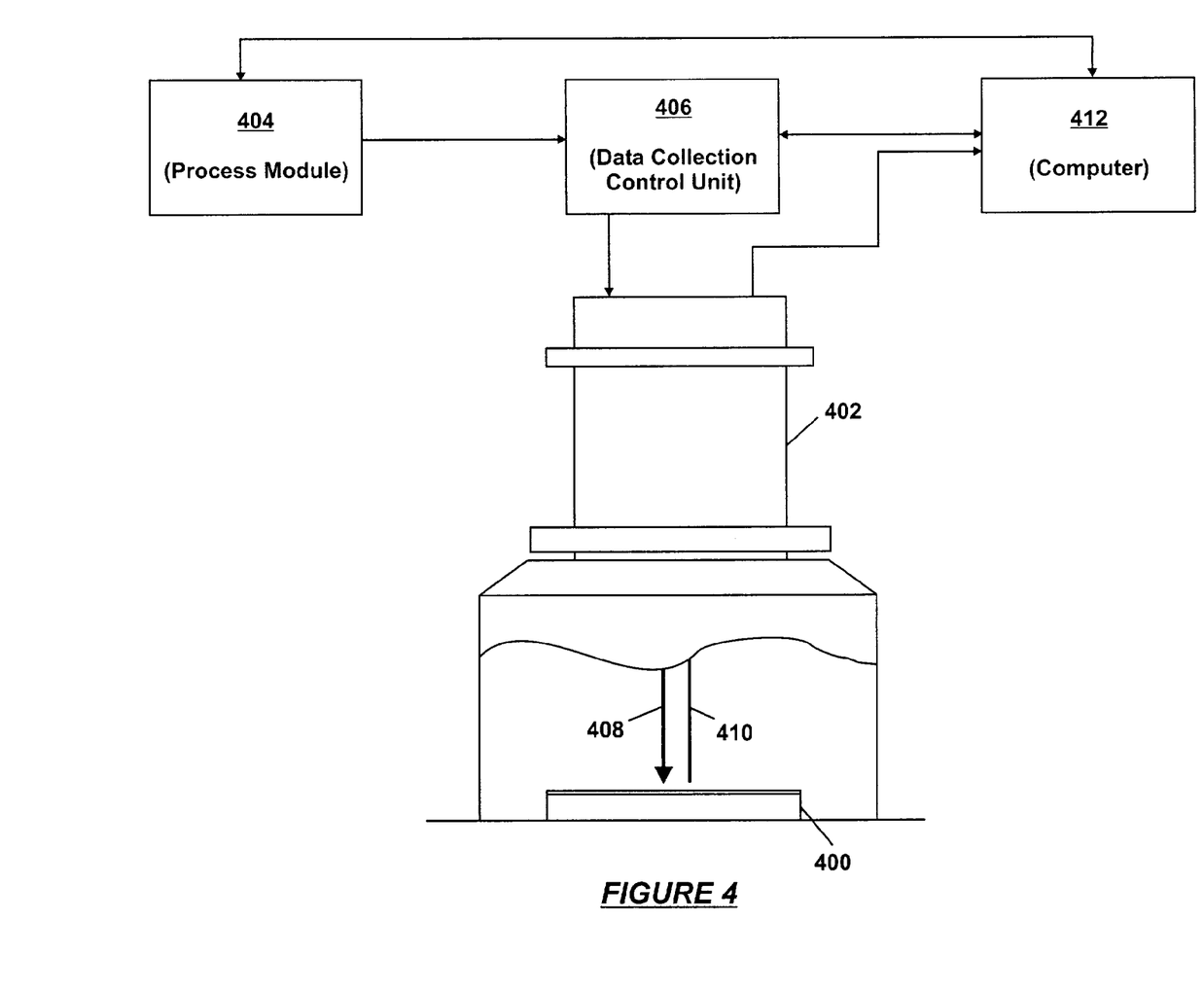
FIG. 4 shows a process setup according to an embodiment of the invention.

For illustration purposes, FIG. 4 shows a patterned substrate 400 that is to be subjected to various processing steps so that features, such as trenches, can be formed. To avoid obscuring the invention, the processing equipment is not shown in FIG. 4. However, it will be obvious to one of skill in the art what processing equipment is needed to form certain features on the substrate 400. For example, if trenches are to be formed via plasma etching, the substrate 400 would be mounted on a chuck (not shown) in a plasma chamber (not shown), and the appropriate equipment for generating the plasma would be provided.

For in-situ monitoring of the substrate state, an optical reflectometer 402 is positioned above the patterned substrate 400. The reflectometer 402 is used to make real-time measurements of reflectance from the substrate 400. The reflectometer includes a light source (not shown) for generating a light beam, a system of optical elements (not shown) for focusing the light beam on the substrate, and a spectrometer (not shown) for detecting and analyzing the spectrum of light reflected from the substrate. In one embodiment, the light source in the reflectometer 402 is a broadband light source. The operating wavelength band of the light source is selected to be in the region where sensitivity to the parameters of interest is heightened. Generally speaking, a broader range is more useful. In one example, the wavelength range of the light source is 190 to 1000 nm.

FIG. 4 shows a process module 404 that controls processing of the patterned substrate 400. At the start of substrate processing, the process module 404 sends a signal to a data collection control unit 406 to trigger operation of the reflectometer 402. When the reflectometer 402 is triggered, a light beam 408 is generated by the light source in the reflectometer 402 and directed to strike the patterned substrate 400 at normal incidence. The spectrometer in the reflectometer 402 detects the light beam 410 reflected at normal incidence from the substrate 400. The spectrometer analyzes the reflected light beam 410 and sends data representative of the reflectance spectrum to a computer 412 for further analysis. The process module 404, the data collection control unit 406, and the computer 412 all communicate with one another too.

The computer 412 includes a model for calculating reflectance of the patterned substrate 400 and a non-linear regression routine that searches for a set of parameterized parameters that provides an optimal match between the modeled reflectance and the reflectance data obtained from the reflectometer 402. It must be noted that as an alternative to the non-linear regression technique, a technique such as multivariate regression analysis or neural net matching might be used to extract the set of optimal parameters. A model for calculating reflectance of a patterned substrate has been described above. The set of parameterized parameters can be mapped to several key quantities of interest, such as film thicknesses and etch depths.

Figure 5A:
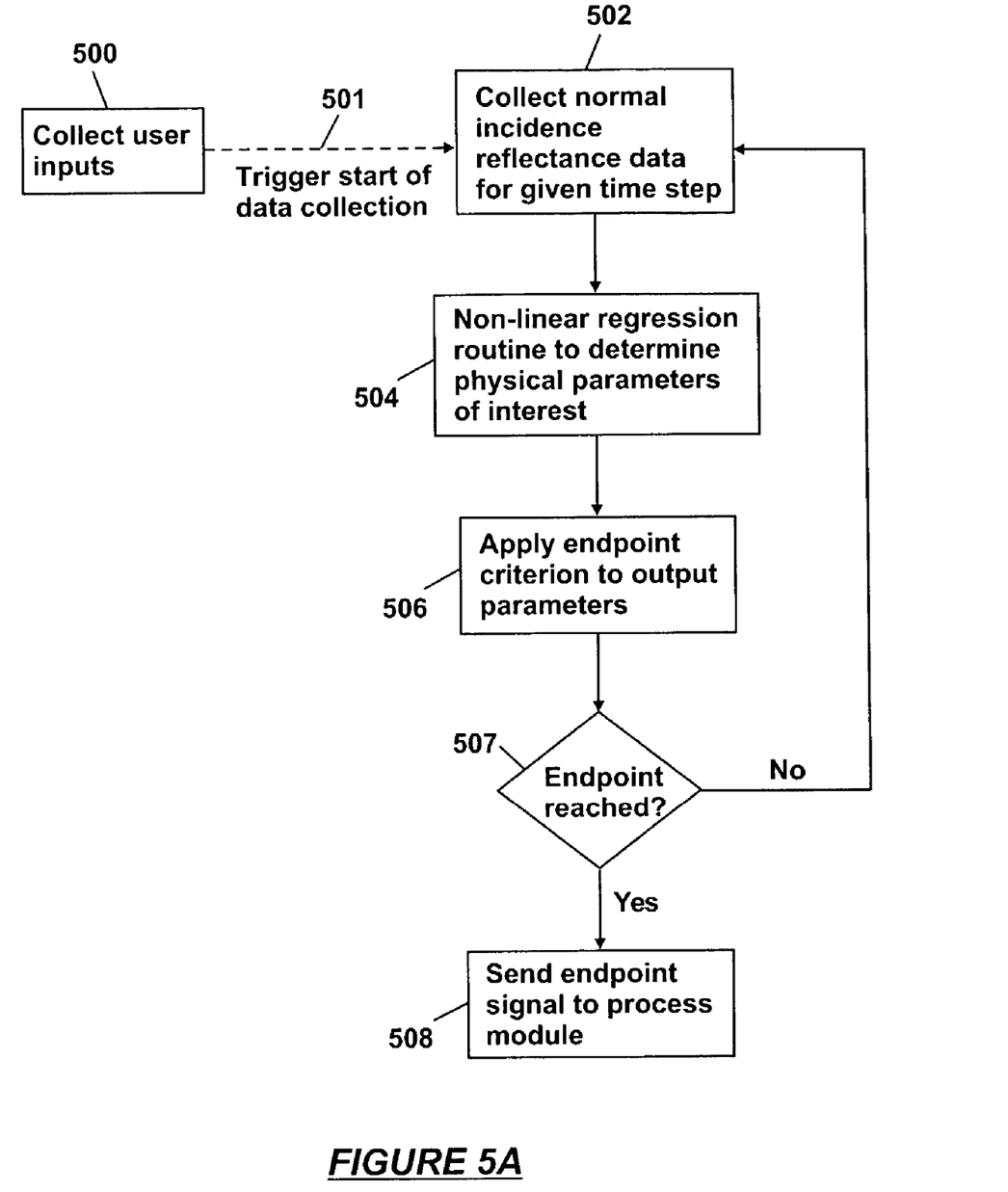
FIG. 5A is an overview of a process for detecting an endpoint in patterned substrate processing step according to an embodiment of the invention.

FIG. 5A is an overview of a process for detecting an endpoint in patterned substrate processing step according to an embodiment of the invention. First, a set of user inputs are collected which contain information necessary to set up the endpoint detection algorithm (500). After collecting the user inputs, data collection is triggered (501). Normal incidence reflectance data is collected from the substrate over a given time interval (502). After collecting the reflectance data, a non-linear regression routine is used to compute a set of parameterized parameters that provides the closest match between the reflectance data and the modeled reflectance of the substrate (504). Then, an endpoint criterion is applied to the parameters (506). For an etching process, for example, an endpoint criterion could be whether the etch depth is greater than or equal to the target etch depth. The system checks whether the endpoint criterion is satisfied (507). If the endpoint criterion is satisfied, a signal indicating a process endpoint is sent to the process module (508). Otherwise, the system returns to step 502.

Figure 5B:
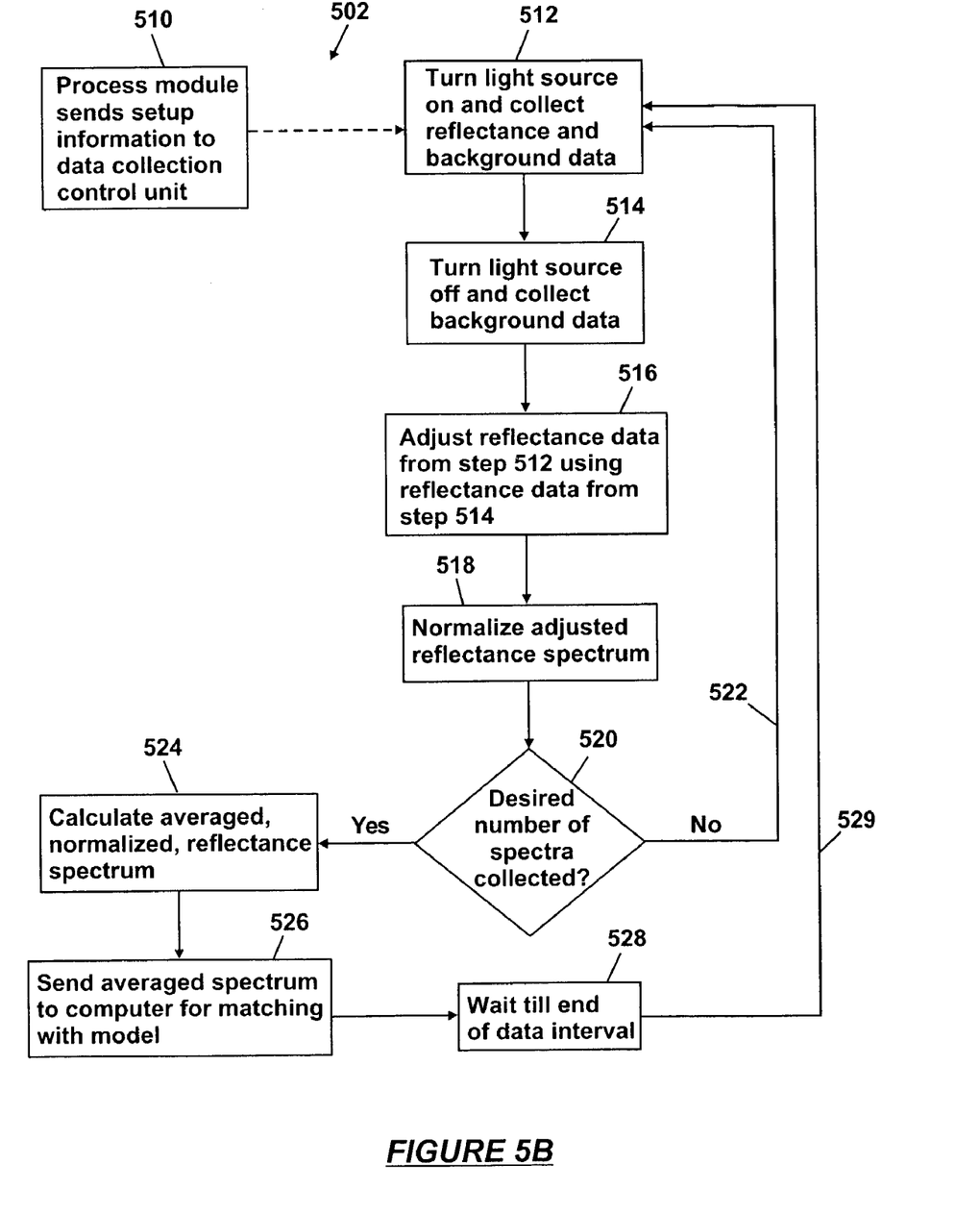
FIG. 5B is an overview of a process for collecting normal incidence reflectance data according to an embodiment of the invention.

FIG. 5B is a flowchart elaborating on step 502 of FIG. 5A, i.e., normal incidence reflectance data collection in-situ. One objective is to improve a high-quality reflectance signal even in the presence of significant background light levels such as the emission from a luminous plasma. Prior to the start of data collection, the process module (404 in FIG. 4) informs the data collection control unit (406 in FIG. 4) about how the data should be collected and calibrated (510). For example, the process module tells the data collection control unit how often to collect the reflectance data from the substrate and the number of reflectance spectra to collect for each time step. The process module also gives the data collection control unit a baseline reflectance spectrum, typically a bare silicon reflectance spectrum, for calibration of the measured reflectance spectra. The bare silicon reflectance spectrum is collected prior to processing the substrate.

When the data collection control unit (406 in FIG. 4) receives instruction to start collecting data, the light source in the reflectometer (402 in FIG. 4) is turned to the ON position to generate a light beam and the spectrometer in the reflectometer collects reflectance data from the substrate (512). Then, the light source is turned to the OFF position and the spectrometer again collects reflectance data from the substrate (514). When the light source is in the OFF position, the data collected by the spectrometer is due to detector noise and other background light sources different from the light source in the reflectometer. For example, in plasma etching, this background light source would be the plasma emissions. The next step is to subtract the reflectance data obtained in step 514 from the reflectance data obtained in step 512 to remove the contribution of the detector noise and background light sources (516).

The corrected reflectance spectrum is normalized by the baseline spectrum (518). Then, the system checks if the desired number of spectra has been collected for the current time step (520). If the desired number of spectra has not been collected, the system returns to step 512 and starts collecting data for another reflectance spectrum (522). If the desired number of spectra has been collected, the system computes an average of the collected spectra to obtain an averaged, normalized, reflectance spectrum (524). The averaged spectrum is sent to the computer (412 in FIG. 4) for matching with the model of the substrate (526). After sending the averaged spectrum to the computer, the system waits for the end of the current time step (528). At the end of the current time step, the system returns to step 512 to start collecting data for the next time step (529).

Figure 5C:
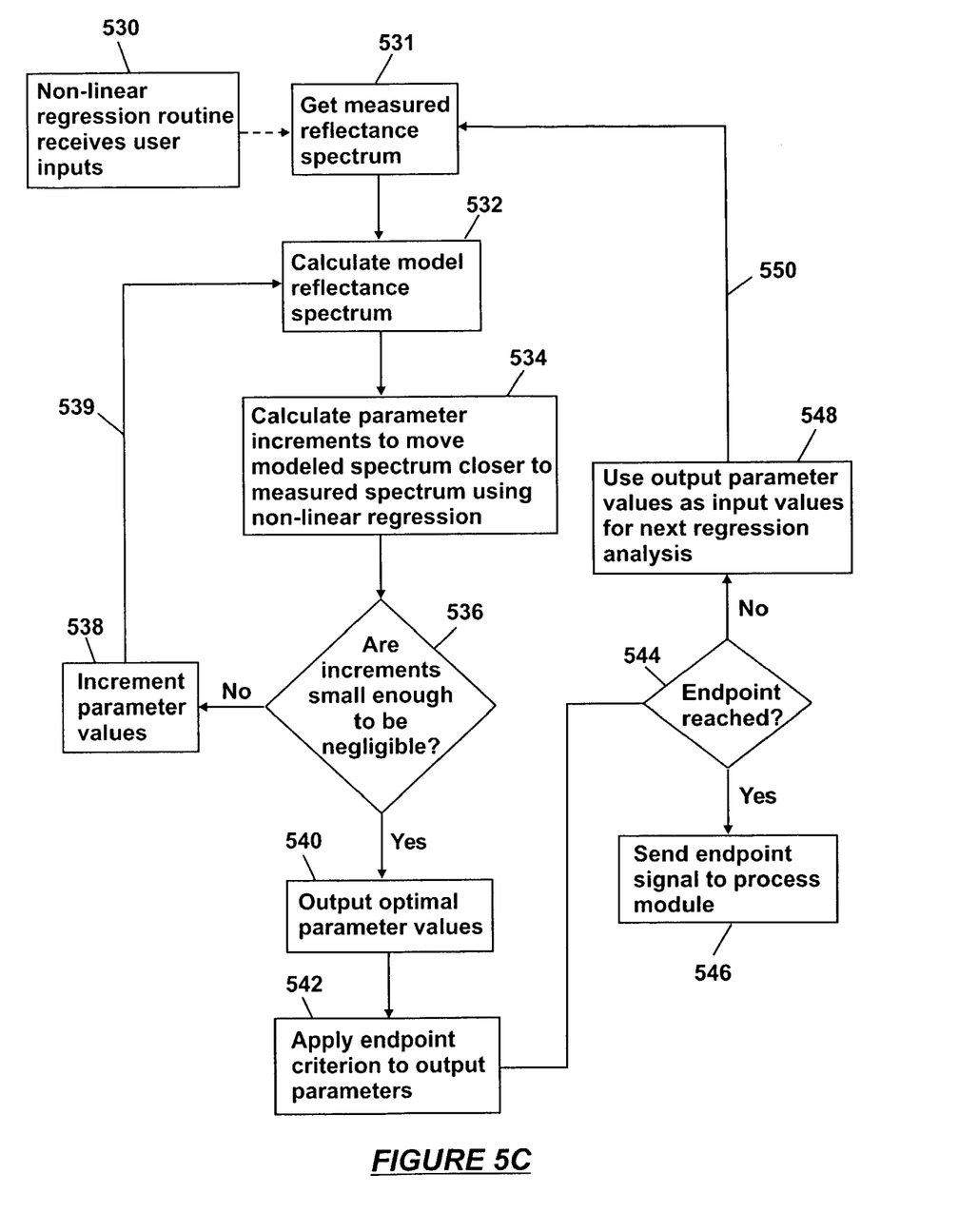
FIG. 5C is an overview of a process for matching measured reflectance spectrum to modeled reflectance spectrum according to an embodiment of the invention.

FIG. 5C is a flowchart elaborating on step 504 of FIG. 5A, i.e., non-linear regression analysis. One objective is to quickly reach a converged set of parameter values by incrementally stepping the parameter values in the appropriate direction through the parameter space till the solution is reached. Prior to start of the non-linear regression analysis, user inputs are received by the non-linear regression routine (530). The user inputs include initial guesses for the parameters to be determined by matching the measured reflectance spectrum to the modeled reflectance spectrum. The non-linear regression routine also receives the (averaged) measured reflectance spectrum (531). Next, the modeled reflectance spectrum is calculated using equations (1) and (2) and the initial guesses included in the user inputs (532). Then, the non-linear regression routine is used to calculate increments to the parameters in equations (1) and (2) to move closer to the best match between the measured reflectance spectrum and the modeled reflectance spectrum (534). The parameters in equations (1) and (2) are the layer thicknesses, etch depths, the weighting factors w, and the coupling factors $\alpha$, which can be functions of the free-space wavelength $\lambda_0$.

The system checks whether the increments calculated in step 534 are small enough to be negligible (536). If the increments are not small enough to be negligible, the system increments the values of the parameters and returns to step 532 to recalculate the modeled spectrum using the new parameter values (538). If the increments are small enough to be negligible, the system outputs the optimal parameter values (540). The physical parameters of interest, e.g., trench depth, are extracted from the optimal parameter values (542). Then, an endpoint criterion is applied to the physical parameters. For example, an endpoint criterion could be that the trench depth is within a certain tolerance from the target depth. The algorithm checks if the endpoint criterion is satisfied (544). If the endpoint criterion is satisfied, a signal is sent to the process module (546). If the endpoint criterion is not satisfied, the next measured reflectance spectrum is obtained and the non-linear regression analysis is repeated (548). The parameter values obtained for the current time step are used as initial guesses for the next non-linear regression analysis (550) to speed up the non-linear regression routine.

Although not explicitly stated at step 532, it should be clear that the user inputs also include information about how to subdivide the substrate into laterally-distinct areas or thin-film stacks. The user inputs also include optical properties of each thin-film stack so that the reflected fields of each thin-film stack can be calculated, as previously described. Before the start of each regression analysis, the reflected fields are recomputed because the structure of the thin-film stacks may have changed during processing of the substrate, consequently resulting in changes in the values of the weighting factors w and the coupling factors $\alpha$ (i.e., in equations (1) and (2) above).

In one embodiment, the invention uses a modified version of a non-linear regression technique called the Levenberg-Marquardt Compromise to quickly and accurately locate optimal values of key parameter starting from the initial guesses of the parameter values. Although, the Levenberg-Marquardt Compromise technique is the preferred technique, other techniques, such as multivariate regression analysis and neural net approaches, may also be employed to extract key parameters of interest.

Figure 6A:
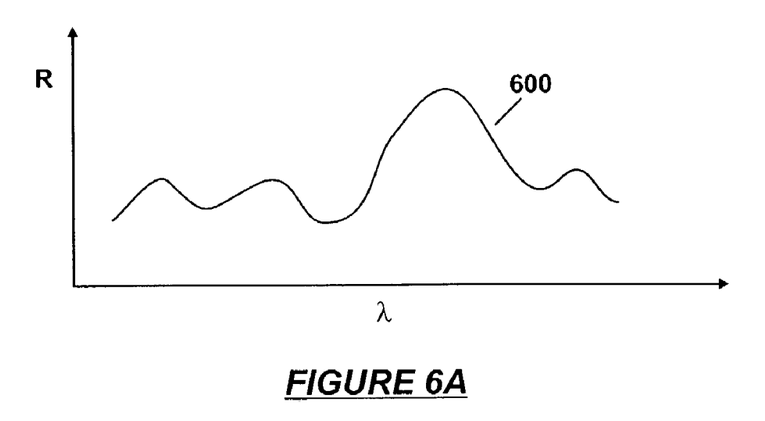
FIG. 6A is a schematic of a measured reflectance spectrum.
Figure 6B:
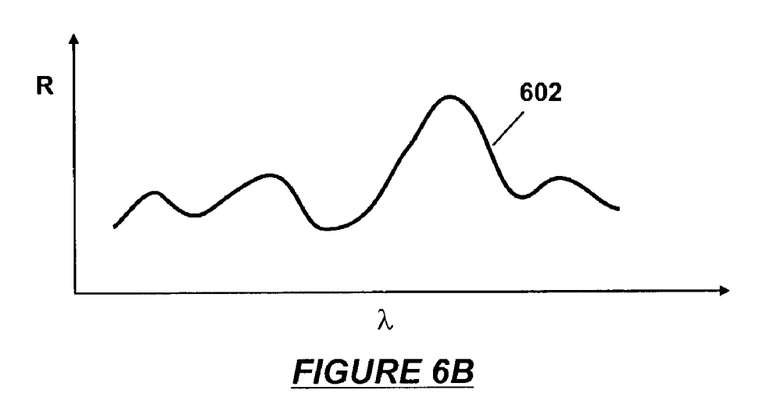
FIG. 6B is a schematic of a modeled reflectance spectrum.
Figure 6C:
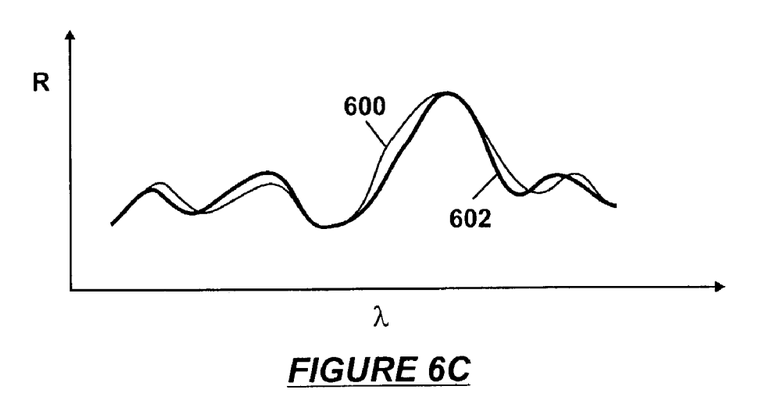
FIG. 6C compares the measured reflectance spectrum of FIG. 6A to the modeled reflectance spectrum of FIG. 6B.

To illustrate how the non-linear regression routine works, FIG. 6A shows a measured reflectance spectrum 600 and FIG. 6B shows a modeled reflectance spectrum 602 computed using initial guesses from user inputs. The first step in the non-linear regression routine is to calculate a least squares difference error metric between the two reflectance spectra 600, 602. FIG. 6C shows the measured reflectance spectrum 600 superimposed on the modeled reflectance spectrum 602. The least squares difference is computed by taking several points across the wavelength range, calculating the vertical difference between the spectra 600, 602 at each point, and summing the square of the differences at all the points. The least squares difference error metric is then used to determine the increments for the parameter values.

So far, the description of the non-linear regression analysis above is standard. Now, what happens in many cases is that a lot of the parameters that are not of interest cause significant changes in the entire modeled spectrum while the parameters of interest cause changes in small regions of the modeled spectrum. To allow the parameter values of interest to be located quickly and accurately, the differences in the regions of the spectrum where the parameters of interest are expected to make a difference are amplified by a factor, e.g., $(1+\gamma_i)$, prior to summing the square of the differences at all the points. Thus, the least squares difference error is larger if the differences in the region of interest are larger. A constant or weighting factor may also be applied to the amplification factor to further bias the least squares difference error.

As can be appreciated from the above, the invention provides several advantages. For example, a patterned substrate having a random array of features can be monitored in-situ using a method of the invention. The invention provides a robust model that can be used to calculate reflectance of the patterned substrate and from which parameters of interest related to the processing of the substrate can be extracted. The model can accommodate incoming material variations, such as layer thicknesses, starting trench depth variation, and differences in pattern density and substrate orientation. The invention uses a biased non-linear regression technique to focus on key parameters of interest much more accurately, thus improving the sensitivity of the system.

While the invention has been described in terms of several preferred embodiments, there are alterations, permutations, and equivalents which fall within the scope of this invention. For example, other techniques can be used to match the measured reflectance spectrum to the modeled reflectance spectrum besides the Levenberg-Marquardt Compromise. It is therefore intended that the following appended claims be interpreted as including all such alterations, permutations, and equivalents as fall within the true spirit and scope of the invention.

What is claimed is:

1. A method of determining a parameter of interest during fabrication of a patterned substrate, comprising:
    illuminating at least a portion of the patterned substrate with a normal incident light beam;
    obtaining a measured net reflectance spectrum of the portion of the patterned substrate from a normal reflected light beam;
    calculating a modeled net reflectance spectrum of the portion of the patterned substrate as a weighted incoherent sum of reflectances from $n \geq 1$ different regions constituting the portion of the patterned substrate, wherein the reflectance of each of the n different regions is a weighted coherent sum of reflected fields from $k \geq 1$ laterally-distinct areas constituting the region; and
    determining a set of parameters that provides a close match between the measured net reflectance spectrum and the modeled net reflectance spectrum.

2. The method of claim 1, further comprising extracting the parameter of interest from the set of parameters.

3. The method of claim 1, wherein each laterally-distinct area is modeled as an isotropic, homogeneous thin-film stack.

4. The method of claim 3, wherein calculating the modeled net reflectance spectrum comprises modeling the patterned substrate as having a nominally polarization-independent reflectance.

5. The method of claim 1, wherein calculating the modeled net reflectance spectrum comprises applying a loss factor to the modeled net reflectance that is proportional to non-specular reflection from the portion of the patterned substrate.

6. The method of claim 1, wherein determining the set of parameters comprises calculating a least squares difference error metric between the measured net reflectance spectrum and the modeled net reflectance spectrum and finding the set of parameters that minimizes the error metric.

7. The method of claim 6, further comprising amplifying an effect of a change in the parameter of interest on the error metric.

8. The method of claim 6, wherein calculating the modeled net reflectance spectrum comprises receiving as input a set of initial guesses for the set of parameters.

9. The method of claim 1, wherein obtaining the measured reflectance spectrum comprises obtaining a set of reflectance spectra of the portion of the patterned substrate over a time interval and setting the measured reflectance spectrum to an average of the set of reflectance spectra.

10. A process control method for fabrication of a patterned substrate. comprising:
   illuminating at least a portion of the patterned substrate with a normal incident light beam while processing the patterned substrate;
   obtaining a measured reflectance spectrum of the portion of the patterned substrate over a range of wavelengths;
   calculating a modeled reflectance spectrum of the portion of the patterned substrate over a range of wavelengths as a weighted incoherent sum of reflectances from $n \geq 1$ different regions constituting the patterned substrate, wherein the reflectance of each of the n different regions is a weighted coherent sum of reflected fields from $k \geq 1$ laterally-distinct areas constituting the region;
   determining a set of parameters that provides a close match between the measured reflectance spectrum and the modeled reflectance spectrum;
   deriving a parameter of interest from the set of parameters; and
   signaling an endpoint in the processing of the patterned substrate if the value of the parameter of interest satisfies a predetermined endpoint criterion.

11. The process control method of claim 10, wherein calculating the modeled net reflectance spectrum comprises applying a loss factor to the modeled net reflectance that is proportional to non-specular reflection from the patterned substrate.

12. The process control method of claim 10, wherein determining the set of parameters comprises calculating a least squares difference error metric between the measured net reflectance spectrum and the modeled net reflectance spectrum and finding the set of parameters that minimizes the error metric.

13. The process control method of claim 12, further comprising amplifying an effect of a change in the parameter of interest on the error metric.

14. A method for determining a vertical dimension of a feature on a patterned substrate, comprising:
   illuminating at least a portion of the patterned substrate including the feature with a normal incident light beam;
   obtaining a measured net reflectance spectrum of the portion of the patterned substrate from a normal reflected light beam;
   calculating a modeled net reflectance spectrum of the portion of the patterned substrate as a weighted incoherent sum of reflectances from $n \geq 1$ different regions constituting the portion of the patterned substrate, wherein the reflectance of each of the n different regions is a weighted coherent sum of reflected fields from $k \geq 1$ laterally-distinct areas constituting the region;
   determining a set of parameters that provides a close match between the measured net reflectance spectrum and the modeled net reflectance spectrum; and
   extracting the vertical dimension of the feature from the set of parameters.

15. The method of claim 14, wherein each laterally-distinct area is modeled as a thin-film stack.

16. The method of claim 15, wherein calculating the modeled net reflectance spectrum comprises modeling the patterned substrate as having a nominally polarization-independent reflectance.

17. The method of claim 14, wherein calculating the modeled net reflectance spectrum comprises applying a loss factor to the modeled net reflectance spectrum that is proportional to non-specular reflection from the portion of the patterned substrate.

18. The method of claim 14, wherein determining the set of parameters comprises calculating a least squares difference error metric between the measured net reflectance spectrum and the modeled net reflectance spectrum and finding the set of parameters that minimizes the error metric.

19. The method of claim 18, further comprising amplifying an effect of a change in the vertical dimension of the feature on the error metric.

20. The method of claim 18, wherein calculating the modeled net reflectance spectrum comprises receiving as input a set of initial guesses for the set of parameters.

21. The method of claim 1 wherein the weighted incoherent sum of reflectances is $$R = w_1(\lambda_0)|E_1|^2 + w_2(\lambda_0)|E_2|^2 + \Lambda + w_n(\lambda_0)|E_n|^2$$

where R is the net reflectance measured, $E_n$ are the individual incoherently adding field terms, and $w_n(\lambda_0)$ are the weighting factors for the incoherently adding terms.

22. The method of claim 1 wherein the weighted coherent sums of reflected fields is $$E_i = \alpha_1(\lambda_0)E_{c1} + \alpha_2(\lambda_0)E_{c2} + \Lambda + \alpha_k(\lambda_0)E_{ck}$$

where $\alpha_k(\lambda_0)$ are the weighting factors for coherently adding field terms $E_{ck}$.

* * * * *